United States Patent [19]

Modak et al.

[11] Patent Number: 5,917,033
[45] Date of Patent: Jun. 29, 1999

[54] STRUCTURE BASED DESIGN OF INHIBITORS OF HIV-1 REVERSE TRANSCRIPTASE

[75] Inventors: Mukund J. Modak, River Edge; Prem N. S. Yadav, Scotch Plains; Janardan S. Yadav, Edison, all of N.J.

[73] Assignee: University of Medicine & Dentistry of New Jersey, Piscataway, N.J.

[21] Appl. No.: 08/550,675

[22] Filed: Oct. 31, 1995

[51] Int. Cl.$^6$ .......................... A61K 31/55; C07D 471/14
[52] U.S. Cl. .......................... 540/487; 540/495; 540/557; 514/220; 514/81
[58] Field of Search ....................... 540/487, 495

[56] References Cited

U.S. PATENT DOCUMENTS 5,571,912  11/1996  Grozinger et al. ..................... 540/495
5,620,974   4/1997  Hargrave et al. ..................... 540/495

*Primary Examiner*—Robert T. Bond
*Attorney, Agent, or Firm*—Richard R Muccino

[57] ABSTRACT

The present invention pertains to a method for designing inhibitors of enzyme human immunodeficiency virus type 1 reverse transcriptase which comprises the steps of:

(a) providing a three dimensional model of the receptor site in the prepolymerization complex of the p66 subunit of enzyme human immunodeficiency virus type 1 reverse transcriptase and a known nonnucleoside inhibitor;

(b) locating the conserved residues in the p66 subunit which constitute the nonnucleoside inhibitor binding pocket; and (c) designing a new nonnucleoside inhibitor which possesses complementary structural features and binding forces to the residues in the p66 subunit nonnucleoside inhibitor binding pocket.

7 Claims, 5 Drawing Sheets

Nevirapine

BHAP

TIBO

α-APA

STRUCTURE BASED DESIGN OF INHIBITORS OF HIV-1 REVERSE TRANSCRIPTASE

BACKGROUND OF THE INVENTION

1. Field of the Invention

The present invention pertains to a method for designing inhibitors of enzyme human immunodeficiency virus type 1 reverse transcriptase. More particularly, the method comprises the steps of (a) providing a three dimensional model of the receptor site in the prepolymerization complex of the p66 subunit of enzyme human immunodeficiency virus type 1 reverse transcriptase and a known nonnucleoside inhibitor; (b) locating the conserved residues in the p66 subunit which constitute the nonnucleoside inhibitor binding pocket; and (c) designing a new nonnucleoside inhibitor which possesses complementary structural features and binding forces to the residues in the p66 subunit nonnucleoside inhibitor binding pocket.

2. Description of the Background

The disclosures referred to herein to illustrate the background of the invention and to provide additional detail with respect to its practice are incorporated herein by reference. For convenience, the disclosures are referenced in the following text and respectively grouped in the appended bibliography.

Acquired immunodeficiency syndrome (AIDS) is believed to be caused by the human immunodeficiency virus (HIV). Human immunodeficiency virus is a retrovirus which replicates in a human host cell. The human immunodeficiency virus appears to preferentially attack helper T-cells (T-lymphocytes or OKT4-bearing T-cells). When the helper T-cells are invaded by the virus, the T-cells become a human immunodeficiency virus producer. The helper T-cells are quickly destroyed causing the B-cells and other T-cells, normally stimulated by helper T-cells, to no longer function normally or produce sufficient lymphokines and antibodies to destroy the invading virus or other invading microbes.

Although the human immunodeficiency virus does not necessarily cause death, the virus generally causes the immune system to be so depressed that the human develops secondary infections such as herpes, cytomegalovirus, pneumocystis carinni, toxoplasmosis, tuberculosis, other mycobacteria, and other opportunistic infections. Kaposi's sarcoma, lymphomas, and cervical cancer may also occur. Some humans infected with the human immunodeficiency virus appear to live with little or no symptoms, but appear to have persistent infections, while others suffer mild immune system depression with symptoms such as weight loss, malaise, fever, and swollen lymph nodes. These syndromes have been called persistent generalized lymphadenopathy syndrome (PGL) and AIDS related complex (ARC) and generally develop into AIDS. Humans infected with the AIDS virus are believed to be persistently infective to others.

Human immunodeficiency virus is an extremely heterogeneous virus. The clinical significance of this heterogeneity is evidenced by the ability of the virus to evade immunological pressure, survive drug selective pressure, and adapt to a variety of cell types and growth conditions. A comparison of isolates among infected patients has revealed significant diversity, and within a given patient, changes in the predominant isolate over time have been noted and characterized. In fact, each patient infected with human immunodeficiency virus harbors a "quasispecies" of virus with a multitude of undetected viral variants present and capable of responding to a broad range of selective pressures, such as those imposed by the immune system or antiviral drug therapy. Therefore, diversity is a major obstacle to pharmacologic or immunologic control of human immunodeficiency virus infection. Human immunodeficiency virus infection has multiple mechanisms to maximize its potential for genetic heterogeneity. These mechanisms result in an extremely diverse population of virus capable of responding to a broad range of selective pressures, including the immune system and antiretroviral therapy, with the outgrowth of genetically altered virus.

When a patient with human immunodeficiency virus infection is initiated on antiretroviral therapy, there is generally a virologic response characterized by declining viremia and antigenemia. Unfortunately, the currently available antiretroviral agents which have undergone clinical evaluation have only limited benefit because most patients will ultimately have evidence of worsening disease and increasing viral burden. This progression often occurs in association with the emergence of drug-resistant human immunodeficiency virus. For example, most patients who are treated with 3'-azido-3'-deoxythymidine (AZT) will have initial evidence of improvement of clinical and laboratory parameters of human immunodeficiency virus infection. The duration of this benefit varies from patient to patient and is likely to be disease stage related. Ultimately, however, most patients will have progressive disease and genotypic or phenotypic evidence of the appearance of AZT-resistant human immunodeficiency virus. Since clinical failure and the appearance of virus with high level resistance to AZT both occur with evidence of increasing levels of viremia and changes in viral tropism, it has been difficult to ascribe the clinical failure solely to the development of AZT resistance. Nevertheless, it seems likely that AZT resistance ultimately contributes to the clinical failure seen in most patients receiving prolonged AZT therapy.

Enzyme human immunodeficiency virus type 1 (HIV-1) reverse transcriptase (RT) is critical for the replication of HIV, which is the causative agent of acquired immunodeficiency syndrome (Goff, 1990). This enzyme (HIV-1 RT) plays a crucial role in the virus life cycle and is responsible for the conversion of the single-stranded RNA viral genome into double stranded DNA (Goff, 1990) (Furfine & Reardon, 1991). This DNA subsequently integrates into the host nucleus and through the normal metabolic pathway is able to produce progeny virus. Because of the distinct function of the reverse transcriptase in the virus life cycle, it is one of the most important targets in antiviral therapy. Two pharmacological classes of inhibitor molecules, i.e., nucleoside and nonnucleoside, have been found to be effective in halting the enzymatic function of the reverse transcriptase (Larder, 1993). Nucleoside inhibitors such as AZT (zidovudine, azidothymidine), ddC (Zalcitabine, 2', 3'-dideoxycytidine, Hivid), ddI (didanosine, 2', 3'-dideoxyinosine, Videx), and d4T (Stavudine, 2', 3'-didehydro-2', 3'-dideoxythymine) are chemically similar to the normal nucleosides and therefore can be converted to their triphosphate form and then used in the synthesis of DNA during reverse transcription. However, elongation of the DNA chain is blocked since these compounds lack a 3'-OH group which is essential for incorporation of additional nucleotides. Problems of cellular toxicity together with development of drug resistant variants of the virus have compromised the effective utility of these drugs. A number of pharmacologically active nonnucleoside inhibitors (NNI) have been identified. Many of these inhibitors appear highly potent, relatively nontoxic, and specifically inhibit HIV reverse transcriptase. However, the rapid emergence of HIV strains resistant to these compounds in vitro has become a major concern that may affect further development of these types of drugs (Larder, 1993). For example, nevirapine (BI-RG-587, 11-cyclopropyl-5, 11-dihydro-4-methyl-6H-dipyrido[3,2-b:2',3'-e(1,4)diazepin-6-one), TIBO (Tetrahydroimidazo[4,5,1-jk][1,4]benzodiazepin-2(1H)-one), HEPT (1-[(2-hydroxyethoxymethyl)]-6-(phenylthio) thymine), BHAP (bis(heteroaryl)piperazine), and alpha-APA (alpha-anilinophenylacetamide) are highly studied compounds in this class (FIG. 3). Rapid mutations, in some cases within weeks or months, in the HIV-1 RT have been reported upon exposure of HIV-infected cells to these compounds. For example, mutations at Val108Ile, Tyr181Cys, and Tyr188His have been noted with pyridinone resistance, while Val106Ala, Tyr181Cys, and Tyr188Cys have been seen associated with nevirapine resistance (see Table 3).

Recently, the cocrystal structures of reverse transcriptase complexed with different nonnucleoside inhibitor molecules such as nevirapine, alpha-APA, HEPT, and, different derivatives of TIBO, have been determined by Arnold and colleagues (Ding et al., 1995A), (Ding et al., 1995B), and (Ren et al., 1995). All these crystallographic studies show that the chemically diverse class of nonnucleoside inhibitor molecules have common features of binding to reverse transcriptase.

Binding of these inhibitor compounds in reverse transcriptase is largely due to hydrophobic interactions. However, the contribution of individual amino acids in generating binding forces for these compounds is different in each case (Table 2). The shape of the hydrophobic pocket is generated by side chain arrangement of the residues, some of which are highly conserved in the reverse transcriptase class of enzymes and others whose mutations are known to develop resistance to the nonnucleoside class of inhibitor molecules. These observations are supported by several biochemical experiments (Balzarini et al., 1992) (Nunberg et al., 1992) (Schleif et al., 1992). Also, the structure of the unliganded structure (Rodgers et al., 1995) has indicated the rearrangement of positions and side chain conformations of certain amino acid residues which have created the cavity for nonnucleoside inhibitor binding. In the absence of a nonnucleoside inhibitor, there is no cavity in the binding region of the nonnucleoside inhibitor. The binding pocket is generated during the association of the nonnucleoside inhibitor. Drug resistance mutations obviously alter the shape of the nonnucleoside drug binding pocket resulting in the inability of the enzyme to bind a specific drug. Therefore, the identification and the availability of new molecules that will retain the binding specificity to this pocket in both the absence and presence of specific mutations is highly desired.

Many mutations reported to be associated with the nucleoside drug resistance of enzyme human immunodeficiency virus type 1 reverse transcriptase are clustered across the carboxylate triad in the p51 subunit of HIV-1 RT, but not in the catalytically active p66 subunit. This observation indicates some discrete role for the p51 subunit in the development of overall nucleoside drug resistance in HIV. Both nucleoside and nonnucleoside inhibitors have been shown to be quite effective in halting the propagation of HIV in tissue culture cells and in the animal model (Larder, B. A., 1993). A major problem with the continued use of these reverse transcriptase inhibitors has been the emergence of drug resistant mutant viruses (Larder, B. A., et al., 1989) (Kellam, R., et al., (1992). The problem of drug resistance in HIV is somewhat complicated since the resistance to an individual anti-RT drug does not always correlate in vitro with resistance of reverse transcriptase isolated from that strain (Larder, B. A., 1993) although a number of drug resistant HIV strains, isolated from patients on long term treatment, have indeed shown that viral resistance is due to mutations in the gene sequences coding for HIV-1 reverse transcriptase (Fitzgibbon, J. E., et al., (1993). The observed drug resistance has been well correlated to mutation at specific sites in HIV-1 RT. For example, mutations at Met 41, Asp 67, Lys 70, Thr 69, Lys 70, Leu 74, Met 184, Thr 215, and Lys 219 have been found to be associated with AZT and ddI resistance phenotype of HIV-1 (RT Lacey, S. F., et al., (1994) (Martin, J. L., et al., (1993) (St. Clair, M. H., et al., (1987). Recently, some additional mutation sites in HIV-1 RT were found in a strain of HIV that was isolated from a patient who was on a combination chemotherapy (AZT+ddI) for a period of one year (Shafer, R. W., et al., (1994).

An examination of residues conferring resistance to nucleoside inhibitors in the three-dimensional structure of HIV-1 RT showed that the mutation sites are dispersed over the entire finger subdomain of the p66 subunit of HIV-1 RT and that most of these sites are away from the catalytic center (FIG. 1) (Yadav, P. N. S., et al., 1995). The amino-acid side chains of many of these residues in the p66 subunit appear to be exposed to the outer surface, that is away from the cleft and towards the solvent medium, suggesting no direct participation of these residues in the polymerase function of the enzyme. The mechanism by which these mutations confer loss of recognition of nucleoside analogues (azido-or dideoxy-derivatives of dNTP) at the active site of HIV-1 RT has remained unexplained. To clarify the local environment around drug resistance sites in HIV-1 RT, a structural analysis of the regions in HIV-1 RT containing the mutations that confer nucleoside analogue resistance was undertaken. A model of the prepolymerization complex of HIV-1 RT template-primer and dNTP was used to analyze the location of the residues involved (FIG. 1). In contrast to the scattered distribution of mutant sites in the finger subdomain of the p66 subunit, these sites were found to be heavily concentrated in the vicinity of the carboxylate triad in the p51 subunit (FIG. 2).

BRIEF DESCRIPTION OF THE FIGURES AND TABLES

Figure 1:
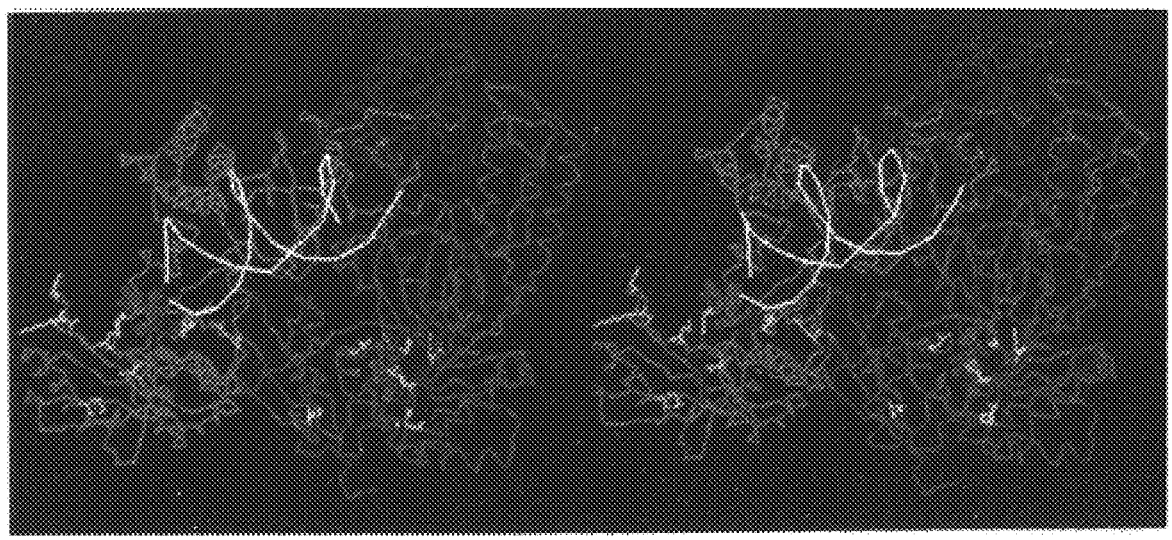
FIG. 1 is a drawing illustrating a stereoview of the complete modelled structure of HIV-1 reverse transcriptase with DNA and AZT triphospahte (AZTTP).

Table 1 lists the amino-acid residues in HIV-1 RT, the mutations of which result in nucleoside analogue resistance, and their C-alpha distances (A) from three catalytically important carboxylates in the p51 and the p66 subunits of reverse transcriptase (Asp 110, Asp 185, Asp 186).

Table 2 shows the HIV-1 RT amino acid residues involved in the binding of nonnucleoside inhibitors (NNIs), that is, residues with at least one atom within a distance of 3.6 Å from the nonnucleoside inhibitor. No mutations were seen for the residues in boldface.

Table 3 shows the contribution of individual amino acids in generating binding forces for inhibitor compounds in reverse transcriptase. Among the residues which constitute the overall binding pocket are Leu100, Lys101, Lys103, Val106, Val179, Tyr181, Tyr188, Val189, Gly190, Phe227, Trp229, Leu234, His235, Pro236, and Tyr318.

Table 4 shows the total energy of complexes and the energy of interactions of a model of nevirapine complexed with reverse transcriptase (Complex O), nevirapine modified with —(CH$_2$)$_4$NH$_2$ complexed with reverse transcriptase ((Complex A)), and nevirapine modified with —(CH$_2$)$_3$NHC(NH)NH$_2$ complexed with reverse transcriptase ((Complex B).

Table 5 shows the free energy of solvation for nevirapine complexed with reverse transcriptase (RT-Nevirapine complex), nevirapine modified with —(CH$_2$)$_4$NH$_2$ complexed with reverse transcriptase (RT-Compound A complex), and nevirapine modified with —(CH$_2$)$_3$NHC (NH)NH$_2$ (RT-Compound B complex) complexed with reverse transcriptase.

SUMMARY OF THE INVENTION

The present invention pertains to a method for designing inhibitors of enzyme human immunodeficiency virus type 1 reverse transcriptase which comprises the steps of:
(a) providing a three dimensional model of the receptor site in the prepolymerization complex of the p66 subunit of enzyme human immunodeficiency virus type 1 reverse transcriptase and a known nonnucleoside inhibitor;
(b) locating the conserved residues in the p66 subunit which constitute the nonnucleoside inhibitor binding pocket; and
(c) designing a new nonnucleoside inhibitor which possesses complementary structural features and binding forces to the residues in the p66 subunit nonnucleoside inhibitor binding pocket.

In another embodiment, the invention relates to an inhibitor of enzyme human immunodeficiency virus type 1 reverse transcriptase which comprises a compound represented by the following formula:

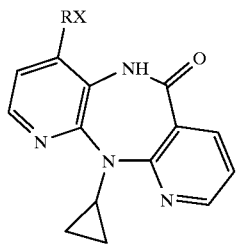

wherein R is an unbranched alkyl or alkenyl group having from 1 to 6 carbon atoms, preferably from 2 to 5 carbon atoms, and more prefereably from 4 to 5 carbon atoms, and X is selected from the group consisting of —OH, —NH$_2$, —NHC(NH)NH$_2$ and —PO(OH)$_2$.

In yet another embodiment, the invention relates to an inhibitor of enzyme human immunodeficiency virus type 1 reverse transcriptase which comprises a compound represented by the following formula:

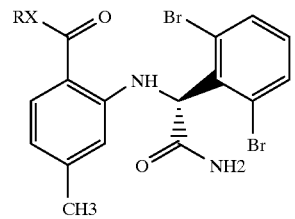

wherein R is an unbranched alkyl or alkenyl group having from 1 to 6 carbon atoms, and X is selected from the group consisting of —OH, —NH$_2$, —NHC(NH)NH$_2$ and —PO(OH)$_2$.

In still yet another embodiment, the invention relates to an inhibitor of enzyme human immunodeficiency virus type 1 reverse transcriptase which comprises a compound represented by the following formula:

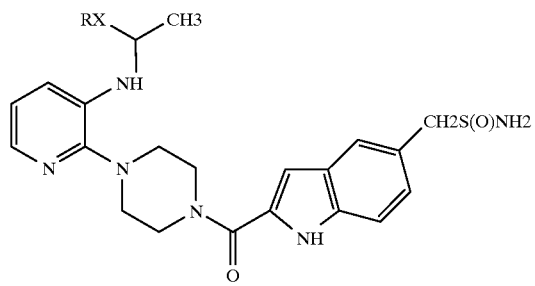

wherein R is an unbranched alkyl or alkenyl group having from 1 to 6 carbon atoms, and X is selected from the group consisting of —OH, —NH$_2$, —NHC(NH)NH$_2$ and —PO(OH)$_2$.

In still yet another embodiment, the invention relates to an inhibitor of enzyme human immunodeficiency virus type 1 reverse transcriptase which comprises a compound represented by the following formula:

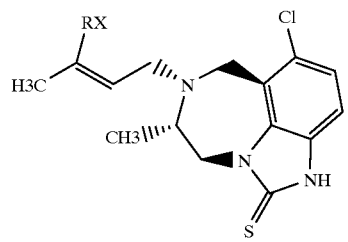

wherein R is an unbranched alkyl or alkenyl group having from 1 to 6 carbon atoms, and X is selected from the group consisting of —OH, —NH$_2$, —NHC(NH)NH$_2$ and —PO(OH)$_2$.

DETAILED DESCRIPTION OF THE INVENTION

In accord with the present invention, applicants have developed a structural based drug design for inhibitor compounds with high specificity towards HIV-1 reverse transcriptase. Crystal structures of HIV-1 reverse transcriptase complexed with different nonnucleoside inhibitors served as a basis for this design. An important feature of the model inhibitors is that the inhibitors retain the structural and electronic specificity of the nonnucleosides to bind to the structurally conserved region and have ability to interact, by virtue of their additional structural motif, with one of the catalytically important and conserved aspartate residues at the active site of the enzyme. Energy of interaction and free solvation energy calculations show that this bidentate class of nonnucleoside inhibitors will have a significantly higher binding affinity than their parent nonnucleoside inhibitor compounds. Accordingly, applicants have provided an atomic outline of fragments which produce bidentate compounds, derivatives of nonnucleoside inhibitors of HIV-1 reverse transcriptase, based on the local three dimensional structure of the receptor site in HIV-1 RT that should prove to be highly specific enzyme inhibitors.

Nucleoside Drug Resistance in HIV-1 Reverse Transcriptase

Figure 2:
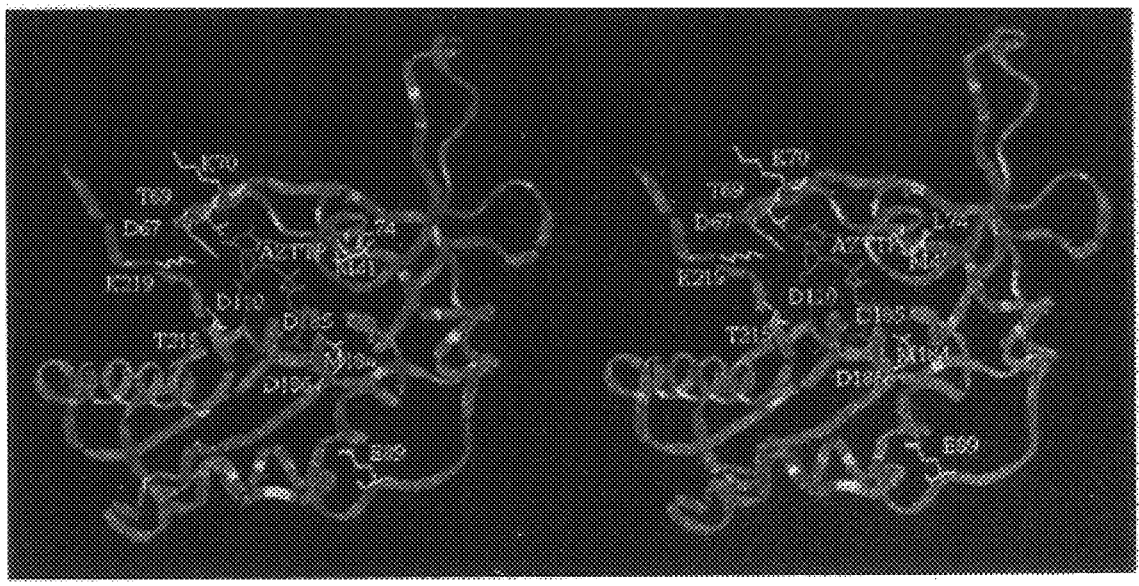
FIG. 2 is a drawing illustrating a stereoview of the proposed binding site for AZTTP in the p51 subunit of HIV-1 reverse transcriptase.
Figure 3:
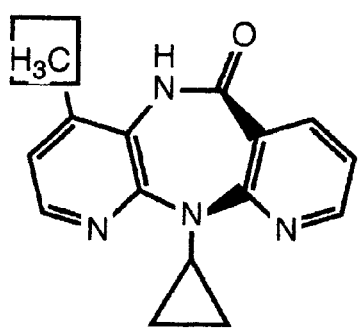
FIG. 3 illustrates the structures of the pharmacologically active nonnucleoside class of inhibitors consisting of nevirapine, TIBO, BHAP, and alpha-APA.
Figure 3:
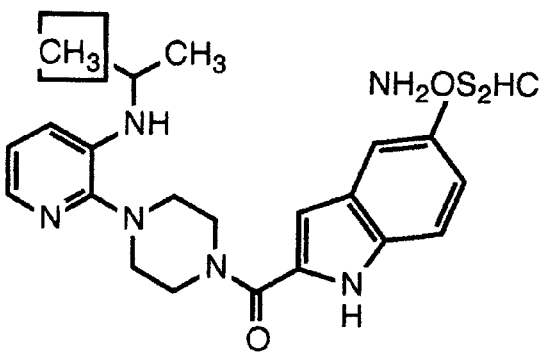
Figure 3:
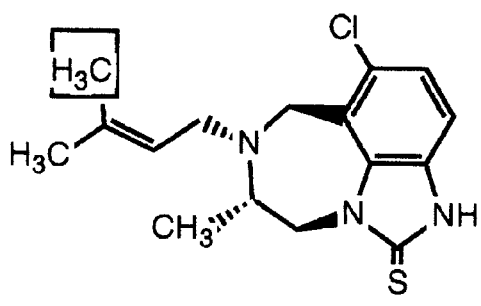
Figure 3:
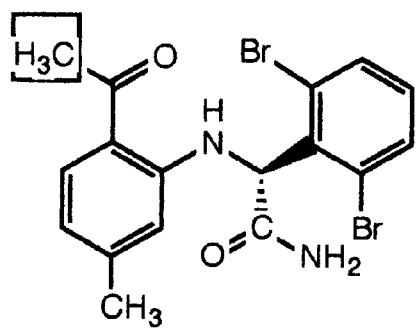

A number of the residues whose mutations confer resistance to ddNTP and AZTTP in the p66 subunit are far from the catalytically important carboxylate triad (FIG. 1). In contrast, in the p51 subunit, these residues appear to be clustered in an area adjacent to the position of the carboxylate triad with the exception of Glu 89 (FIG. 2). In the p51 subunit, Glu 89 does not form a part of the binding pocket. The side-chain orientation of Glu 89 in the p66 subunit appears towards the template binding track and it is likely that mutations of this residue may perturb the template-primer binding such that inhibitor recognition is lost. Nevertheless, mutation of this residue in the p51 subunit has been shown to have significant effects on the $V_{max}$ of HIV-1 RT, suggesting that the so called "inert subunit" modification can exert influence on the functioning of the p66 subunit (Kew, Y., et al., 1994) (Boyer, P. L., et al., 1994). Measurement of the atomic distances between the C-alpha of the individual carboxylate and the mutant residues in both the p51 and p66 subunits confirms this distribution pattern (Table 1). Careful examination of the region encompassing these residues shows that sufficient space exists within the p51 subunit to stereochemically accommodate dNTP/ddNTP. Accordingly, applicants propose that nucleoside substrates and inhibitors may bind to the inert p51 subunit. In FIG. 2, AZTTP, ddGTP, and ddCTP have been tentatively docked in this pocket (only AZTTP is shown). While the triphosphate moiety is facing towards the carboxylate triad and could be bound by a divalent-cation bridge, the residues Met 41, Asp 67, Thr 69, Lys 70, Leu 74, Met 184, Thr 215, and Lys 219 appear to be clustered around the nucleoside moiety of AZTTP. The residues Ala 62, Val 75, Phe 77, Phe 116, and Gln 151, whose mutations caused combined resistance to AZT and ddI (Shafer, R. W., et al., 1994), are also present in the vicinity of the carboxylate triad in p51 but not in p66 (Table 1). The ability of the p51 subunit to bind dNTP has been demonstrated with catalytically competent homodimeric p51 HIV-1 RT (Bavand, M. R., et al., 1993), however, the binding of dNTP/inhibitors that applicants propose would be to the inert p51 subunit.

Recently, the complete three dimensional structure of HIV-1 RT bound to the nonnucleoside inhibitor nevirapine has been solved and the binding site for the nonnucleoside inhibitor has been defined (Smerdon, S. J., et al., 1994). The binding site for nonnucleoside drugs exists only in the p66 subunit (Smerdon, S. J., et al., 1994). Furthermore, HIV-1 RT mutants that exhibit resistance to these inhibitors have been found to contain mutations in residues that contribute to the binding site in the p66 subunit (Smerdon, S. J., et al., 1994). Positions of these residues in the p51 subunit do not permit formation of a stereochemically suitable pocket for nevirapine binding and hence their mutation in this subunit appears inconsequential.

Kinetic studies on the mechanism of inhibition of HIV-1 RT by AZTTP have shown that AZTTP is a competitive inhibitor with respect to dTTP and has similar binding affinity (Km) to HIV-1 RT (Lacey, S. F., et al., 1992). The extremely low $K_1$ value observed for AZTTP (Lacey, S. F., et al., 1992) suggests that factors other than competition with substrate may also play a role in the inhibitory effects of these analogues. The observation that the p51 subunit, exhibits local concentration of the majority of the sites involved in nucleoside resistance across the carboxylate triad may be significant. The proposed presence of a dNTP/ddNTP binding pocket in the p51 subunit may represent the other factor involved in the sensitivity of HIV-1 RT to nucleoside inhibitors and that the mutations in this subunit may be largely responsible for the nucleoside drug resistance in HIV-1 RT.

FIG. 1 is a drawing illustrating a stereoview of the complete modelled structure of HIV-1 reverse transcriptase with DNA and AZTTP. Starting with the C-alpha crystal coordinates (Jacobo-Molina, A., et al., 1993), applicants completed the structure of HIV-1 reverse transcriptase. Completion of the backbone and generation of the side chains was performed using a SYBYL molecular modelling package version 6.0 (Tripos Assoc., St. Louis Mo.). Part of the molecular modelling protocol was similar to the one used for the completion of the Klenow structure (Yadav, P. N. S., et al., 1992). Structural refinement was performed using side-chain conformational search and geometry optimization schemes. Amber charges and Kollman united atom approach was used for energy minimization. The p66 subunit is shown in blue. The large green region represents RNase H domain, while the p51 subunit is shown in cyan (greenish blue). Docking of DNA into the reverse transcriptase structure was based on the positions of P atoms of the phosphate backbone found in the crystal structure (Jacobo-Molina, A., et al., 1993). Docking of dNTP was based on the known requirements for the nucleotidyl transfer reaction catalyzed by DNA polymerases (Pelletier, H., et al., 1994). Positions of two Mg2+metal ions (not shown) were optimized based on their coordinations with the three carboxylates (namely Asp 110, Asp 185, and Asp 186), 3'-O of the primer terminus and triphosphate moiety of dNTP. The positions of the phosphate atom backbone of DNA is shown in magenta. Metal chelated AZTTP was transposed into the p51 subunit of reverse transcriptase considering three carboxylate oxygens (Asp 110, Asp 185, and Asp 186) as reference points. The geometry of the complex was energy refined. Residues whose mutation confer resistance to the nucleoside inhibitors are shown in yellow and AZTTP in red. Green side chains in the active site represent the three catalytically important carboxylate residues.

FIG. 2 is a drawing illustrating a stereoview of the proposed binding site for AZTTP in the p51 subunit of HIV-1 reverse transcriptase. For clarity, the structure consisting of residues Ile 2-Arg 225 is shown in the form of the ribbon diagram (cyan) and the triphosphate moiety of AZTTP (red), is oriented towards the carboxylate triad (green). Note that most of the residues (yellow) whose mutations confer resistance to nucleoside inhibitors are located around the base and sugar moieties of AZTTP.

Table 1 lists the amino-acid residues in HIV-1 RT, the mutations of which result in nucleoside analogue resistance, and their C-alpha distances (A) from three catalytically important carboxylates in the p51 and the p66 subunits of reverse transcriptase (Asp 110, Asp 185, Asp 186).

TABLE 1

| Residue | Asp 110 | | Asp 185 | | Asp 186 | |
|---|---|---|---|---|---|---|
| | p51 | p66 | p51 | p66 | p51 | p66 |
| Met41 | 18.3 | 22.1 | 18.4 | 20.7 | 20.9 | 23.8 |
| Ala62 | 15.1 | 26.5 | 16.7 | 24.7 | 17.2 | 27.6 |
| Lys65 | 12.3 | 22.9 | 16.8 | 22.7 | 15.3 | 24.6 |
| Asp67 | 10.8 | 22.3 | 16.5 | 23.7 | 14.6 | 24.6 |
| Thr69 | 12.1 | 19.7 | 17.1 | 20.4 | 16.5 | 22.0 |
| Lys70 | 13.1 | 23.5 | 17.5 | 24.0 | 17.1 | 25.8 |
| Leu74 | 11.7 | 22.7 | 11.2 | 20.2 | 12.6 | 23.3 |
| Val75 | 14.6 | 24.4 | 12.9 | 21.2 | 14.9 | 24.6 |
| Phe77 | 16.4 | 25.7 | 12.5 | 21.6 | 14.9 | 25.1 |
| Glu89 | 19.4 | 20.7 | 13.7 | 15.4 | 15.8 | 17.6 |
| Phe116 | 13.1 | 14.4 | 11.4 | 11.3 | 14.5 | 14.9 |
| Gln151 | 10.0 | 18.1 | 6.9 | 14.1 | 10.2 | 17.7 |
| Met184 | 9.3 | 5.6 | 3.7 | 3.8 | 5.7 | 5.5 |
| Thr215 | 5.5 | 8.9 | 12.1 | 10.1 | 12.3 | 11.2 |
| Lys219 | 10.8 | 7.1 | 16.5 | 12.1 | 14.4 | 10.7 |

Structure Based Design of Inhibitors of HIV-1 Reverse Transcriptase

Definition of the Nonnucleoside Inhibitor Drug Binding Pocket (NNIBP)

The nonnucleoside inhibitor binding pocket (NNIBP) was assembled by a number of secondary structure elements such as, beta sheet 9, 10, 12, 13, and 15. Among the residues which constitute the overall binding pocket are Leu100, Lys101, Lys103, Val106, Val179, Tyr181, Tyr188, Val189, Gly190, Phe227, Trp229, Leu234, His235, Pro236, and Tyr318 (Table 3). The only residue from the p51 subunit which is a part of the pocket is Glu138. In the crystal structure of the RT-nevirapine complex (Smerdon et al., 1994), residue Tyr319 instead of Tyr318 has been implicated in the nevirapine binding. However, other crystal structure analysis by Ding et.al. (Ding et al., 1995) and Ren et. al. (Ren et al., 1995) have indicated a missassignment in a stretch of residues 314–336 by a shift of one amino acid. Two tyrosines at positions 318 and 319 are present in the primary amino acid sequence of HIV-1 reverse transcriptase. Therefore, Tyr318 at the site of binding was considered. Out of 16 residues mentioned above, only 7–8 residues are directly participating in each nonnucleoside inhibitor binding. Interestingly, amino acid residues Leu100, Lys101, Tyr181, Tyr188, Trp229, and Tyr318 have at least one atom within a distance of 3.6 Å from most of the nonnucleoside inhibitors bound in the pocket (see Table 3). However, their side chain orientations are different in each case. A highly conserved Tyr-Met-Asp-Asp (YMDD) motif is present adjacent to the NNIBP where two catalytically critical carboxylate residues reside. Residues Asp185 and Asp186 constitute the turn for beta sheet hairpin loop while the two tyrosine residues, 181 and 188, which directly bind to the nonnucleoside inhibitor lie at the opposite end of the loop. Though a major part of the pocket is strictly hydrophobic, at the entrance of the pocket there are hydrophilic residues Lys101, Lys103 from p66 and Glu138 from the p51 subunit (Ding et al., 1995).

Out of the residues constituting the NNIBP, commonly occuring natural mutation sites (Table 2) are Leu100-Ile, Lys103-Asn, Val106-Ala, Tyr181-Cys, and Gly190-Glu (Larder, 1992), (Balzarini et al., 1992), (Byrnes et al., 1993), (Bacolla et al., 1993), (Kleim et al., 1993). An important characteristic of this pocket is that residues Phe227, Trp229, Leu234, and Tyr318 are conserved in HIV-1 reverse transcriptase and HIV-2 RT (Johnson et al., 1986) and no viral strains show mutations at these sites. This indicates some discrete role for these residues in the viral replication. The in vitro mutation of Trp229 has shown the DNA polymerase activity significantly impaired (Jacques et al., 1994). Also, it is clear from the crystal structure analysis that the residues mentioned above do not directly participate in the binding of either dNTP or DNA substrates.

Strategy of Designing A New Inhibitor

The strategy for designing new inhibitor molecules was to utilize the binding forces provided by the conserved residues and include other charged areas that are in close atomic vicinity of the NNIBP. The RT-nevirapine complex shows that a region comprising parts of the nevirapine binding site (residue Phe227, Trp229, Leu234) together with neighbouring residues Tyr183, Met184 and Asp186 may constitute a new target site. The aim was to design a compound which would possess complementary structural features to the nonnucleoside inhibitor binding pocket and simultaneously interact with other conserved parts of the extended pocket which is stereochemically feasible in the crystal structures of RT-nonnucleoside inhibitor complexes. Nevirapine was chosen as a lead compound and utilized its receptor site to guide the design of a new compound.

Figure 4:
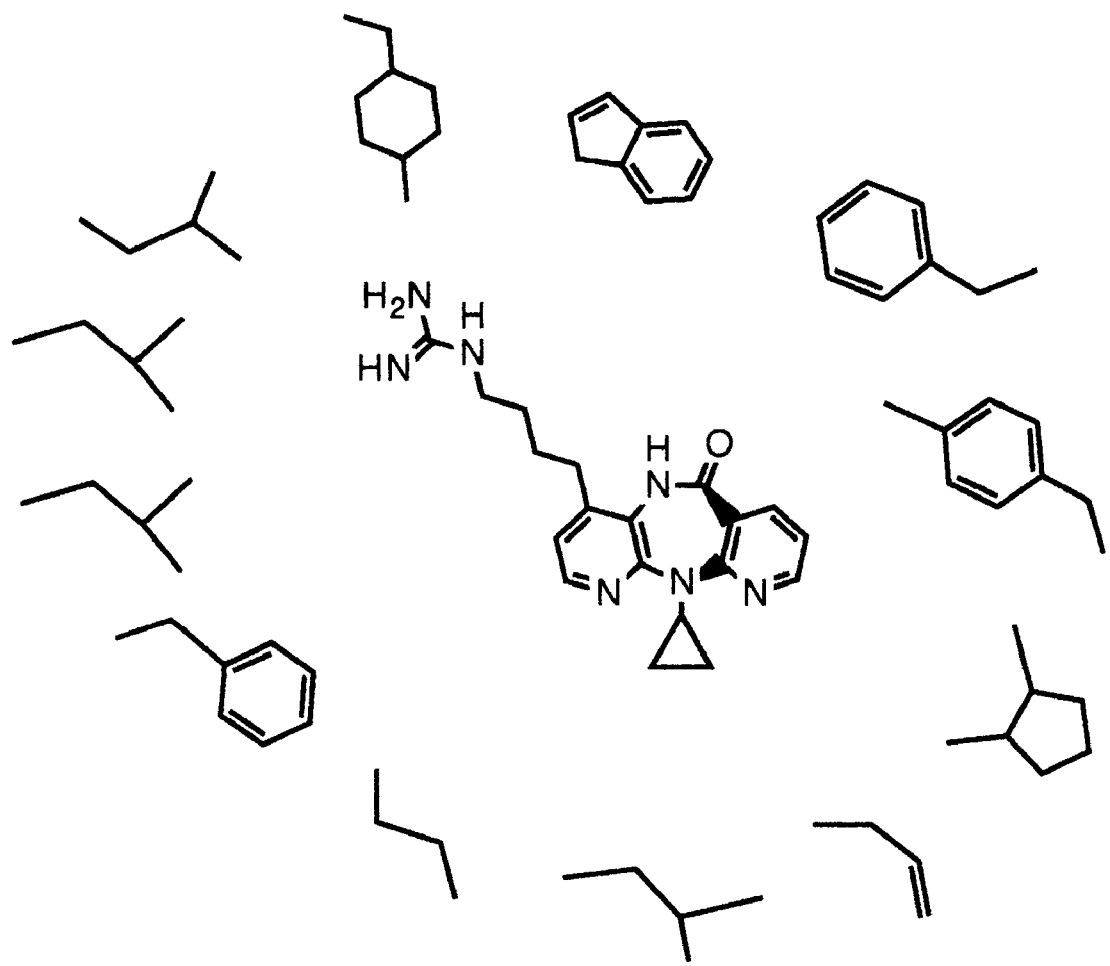
FIG. 4 is a drawing illustrating that the site of substitution of the chain fragment in the inhibitor molecule is common in all known cocrystal structures of nonnucleoside inhibitor-RT complexes.

Analysis of the crystal structures of reverse transcriptase complexed with nevirapine, TIBO, alpha-APA, and HEPT has given an indication of the presence of a site in each compound where a substitution of a hydrocarbon side chain (extension) is possible. This site is located in the wing I (Ding et al., 1995) and faces towards the polymerase active site. Furthermore, compounds which have a larger group or a substitution at this site are found to be better inhibitors (Pauwels et al., 1990). For example, nevirapine, alpha-APA, and TIBO, have the groups $-CH_3$, $-COCH_3$, and $-C(CH_3)_2$, respectively, at a position which is towards the polymerase site. In the crystal structure of reverse transcriptase complexes, the site of substitution falls at a common place (FIG. 4).

Molecular Modeling Protocol

The SYBYL fragment library was used to search for the fragments which could be substituted on the nonnucleoside inhibitor and fit in the NNIBP toward the polymerase active site as contributed by residues Tyr183, Met184, Asp186, and Trp229. In this search, some constraint was placed on atoms which may have a potential to interact at the polymerase active site.

Most of the molecular modeling studies were performed using SYBYL molecular modeling package (Tripos Assoc.) and InsightII (Biosym Technologies). Final geometry optimizations of the ligand molecules and complexes were done using Kollman united approach and MAXIMIN2 minimizer. The energy of interaction was calculated using the following equation:

DELTA $E_{interaction} = E_{complex} - (E_{ligand} + E_{enzyme})$

Solvation energies were calculated using Delphi and Solvation module (version 2.5) of Biosym Technologies. Point charges for ligand molecules were calculated using MOPAC molecular orbital package. The solvation energy for each ligand molecule and enzyme was calculated separately and the contribution of the solvation energy in the interaction free energy was determined by the following equation:

DELTA $G = G_{complex} - (G_{ligand} + G_{enzyme})$

Results and Discussion

As out above, in the crystal structures of various inhibitor complexes, the side chain conformation of amino acid residues constituting the pocket are not rigid but are influenced by the interaction of the inhibitor molecule. It can be deduced from the chemistry of the NNIBP, i.e., interior hydrophobic and exterior hydrophilic or polar, that a suitable fragment should contain a hydrophobic chain with polar or basic end group. A number of branched hydrophobic chains and ring structures was tested. These fragments could not be accommodated in the pocket and generated severe steric hindrance with the surrounding. This observation is in agreement with the experimental observation where a series of TIBO derivatives have been tested for their inhibitory activity (Pauwels et al., 1994). TIBO with a bulky group or ring structure such as a cyclopropyl group substitution have increased the $EC_{50}$ value significantly.

Figure 5:
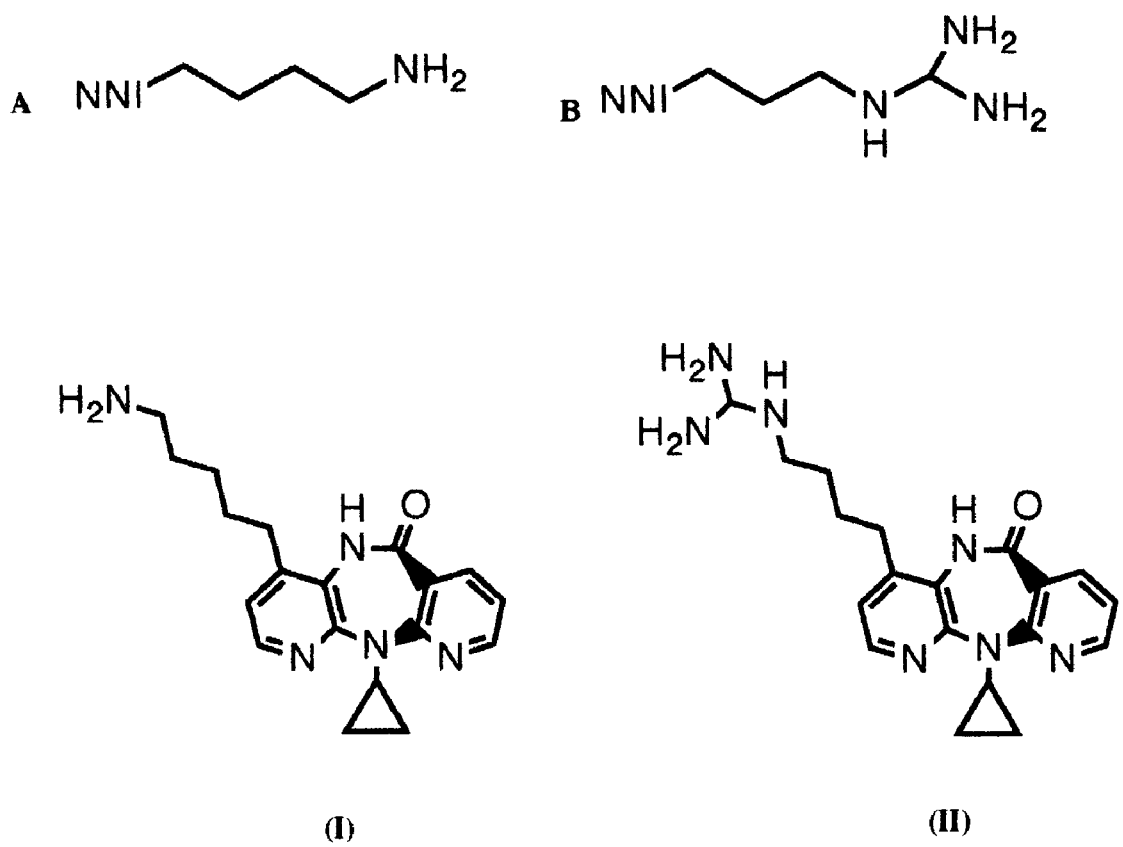
FIG. 5 is a drawing illustrating two fragments which contain the butanyl and propanyl hydrophobic chain and a hydrophilic group at the end, i.e., —$(CH_2)_4NH_2$ and —$(CH_2)_3NHC(NH)NH_2$, which was found to be the best fit in the reverse transcriptase bound structure.

Finally, applicants found two fragments which contain a butanyl and propanyl hydrophobic chain and a hydrophilic group at the end, $-(CH_2)_4NH_2$ and $-(CH_2)_3NHC(NH)NH_2$, respectively. These chains were found to be the best fit in the pocket (FIG. 5). Substitution of these chains in the nonnucleoside inhibitor molecules in the reverse transcriptase bound structure have given a complex structure which is sterically free and energetically more stable than the parent compounds and all these compounds exhibited stereochemical complementarity with the predefined pocket. In addition to the interactions in the parent complexes, the modified regions of these compounds have better interactions particularily with the amino acid residues, Tyr181, Tyr183 (main chain), Asp186, Phe227, Trp229, and Leu234, Tyr318. None of the amino acid residues, except Tyr181, have been selected as a site for drug resistance mutation for the nonnucleoside inhibitor. Also, these amino acid residues are highly conserved in the reverse transcriptase class of enzymes (Ding et al., 1995). This indicates the importance of these amino acid residues in the structural integrity and/or normal polymerase function of the reverse transcriptase enzyme and the virus may not afford to loose these monomers.

As a model, extensive simulation studies were performed on the modified nevirapine complexed with reverse transcriptase. In the following text, the designation (I) was used for nevirapine modified with the sdie chain $—(CH_2)_4NH_2$ and the designation (II) was used for nevirapine modified with the side chain $—(CH_2)_3NHC(NH)NH_2$.

The total energy of the complexes and the energy of interactions are given in Table 4. As a cautionary note, the energy values presented here should not be considered absolute. These values nonetheless provide a comparison of favorable and unfavorable binding interactions within the complexes. RT-(I) and RT-(II) are 36 and 95 kcal/mol, respectively, more stable than RT-Nevirapine complex while the values of interaction energy of enzyme-ligand complexes for RT-nevirapine, RT-(I) and RT-(II) are −30, −73, and −137 kcal/mol, respectively. It may be pointed out here that the additional energy of interaction for two complexes containing modified nevirapine comes from the electrostatic component. The complexes with the modified nevirapine ligands retain the interactions between nevirapine and reverse transcriptase which is mainly due to van der Waal and hydrophobic forces, while electrostatic interactions provide additional binding force. Of the two molecules (I) and (II), the charge associated with the $NH_2$ group and the $NHC(NH)NH_2$ group are +0.70 and +1.24, respectively. More charge indicates better electrostatic interaction. In the present case, the carboxylate group of Asp186 directly interacts with the substituted ligands. Also, the NH group of molecule (II) is at a distance appropriate for hydrogen bonding with the OH group of Tyr181 which provides an additional favorable binding interaction.

The contribution of the free energy of solvation for reverse transcriptase, ligand, and complexes was calculated and may serve as a better measure of binding affinities among the complexes. The relative solvation energy contribution (solvation energy of RT-nevirapine complex was considered as 0 kcal/mol) for complexes RT-(I) and RT-(II) is −25 and −50 kcal/mol, respectively (Table 5). An example of the ratio of solvation energy and binding affinity has been given by Plaxco and Goddard (Plaxco, 1994). In a system of protein DNA complex, the energy of selectivity of 0.9 kcal/mol corresponds to a 5 fold increase in $K_d$. If this ratio holds true for the present system, then the $K_d$ for compound (I) and (II) will be 140 and 280 fold more than that for the parent compound nevirapine.

To determine the effects of substitution of the structural chains on nevirapine, the allowed conformations of the nevirapine moiety were generated in the nevirapine itself and in both substituted nevirapine moieties and the net atomic charge distribution was calculated. The common conformational preference in each compound and the conformational barrier for the nevirapine moiety in the three compounds were found to have similar characteristics. Furthermore, the MNDO (modified neglect of differential overlap) charge calculations showed no significant difference in the net atomic charge on the individual atoms in the nevirapine moiety of these molecules. These observations indicate that modified compounds retain all the structural and electrostatic characteristics of the parent compound and provide additional features for strong affinity towards reverse transcriptase.

The site of substitution of the chain fragment is common in all known cocrystal structures of nonnucleoside inhibitor-RT complexes FIG. 4). These fragments were substituted into the TIBO and alpha-APA complex structures and in addition to the initial interactions between drug and protein, additional interactions between the fragment and protein similar to the one seen in the RT-(I) and RT-(II) complexes were noted. This gave indications that most of the nonnucleoside inhibitors which bind to the NNIBP as defined earlier, when substituted with the designed fragment, will have a stronger binding affinity than the parent compounds.

Drug Resistance

Residues, the mutations of which have been shown to develop resistance to the nonnucleoside inhibitors, are given in Table 2. The mutation of these amino acid residues was modeled by replacing them by their corresponding monomers in the RT-nevirapine, RT-TIBO, and RT-alpha-APA complexes. In most of the cases, natural mutations involve the substitution of relatively smaller side chains. This reduction in the size of the side chains may lead to the loss of specificity of interactions with the specific inhibitor molecules and these changes may not block the pocket. The only exceptions are Leu100Ile, Val179Glu, and Gly190Glu. Substitution at Leu100 to Ile, Val179 to Glu and Gly190 to Glu showed the side chain position at a distance of 1.8, 1.6 and 1.5 Å, respectively, from the TIBO and the substitution of Gly190 to Glu a distance of 1.2 and 2.2 Å from alpha-APA and nevirapine, respectively. However, in another crystal structure, conformations of these side chains are stabilized in a position which do not show steric hindrance with the ligand molecules. These are in agreement with the fact that Val179 mutation to Asp/Glu and Gly190 mutation to Glu are resistance to pyridinone derivatives and not TIBO or nevirapine (Byrnes et al., 1993), (Kleim et al., 1993). This in turn suggests that the mutant enzymes (Val179Glu/Asp and Gly190Glu) do not lose their ability to bind to TIBO or nevirapine. In the crystal structures of RT-TIBO, RT-nevirapine, and RT- alpha-APA complexes, Val106 has significant van der Waal contacts with the ligand molecules. Substitution of Val106 to Ala cannot be in a position to interact with any of the ligand molecules and subsequently confer resistance to these drugs (Larder, 1992) (Richman et al., 1993). Similarly, Tyr181 and Tyr188 may destroy the interactions of the phenyl ring with the drug molecules (Nunberg et al., 1991), (Richman et al., 1991), (Richman et at., 1993), (Balzarini et al., 1993).

These studies indicate that the ability of NNIs to bind or not to bind in the pocket may be related to the size of the pocket which stabilizes the binding of NNIs through hydrophobic or van der Waals interactions. Therefore, it is clear that the enlarged size at a specific site of the pocket is responsible for the resistance to a particular drug and the substitution at NNIs proposed here may not interefere with the binding process in the wild type or mutant enzyme. Instead it may form a more stable complex with both the wild type and mutant so called resistant enzyme.

Since the parent compounds have been shown to have desirable metabolic characteristics, such as physiological absorption and distribution, the addition of these chains would not be expected to change these properties since these groups have been used in many natural products used as drugs, for example, the protein phosphatase 1 and 2A (Schreiber, 1992).

Table 2 shows the HIV-1 RT amino acid residues involved in the binding of nonnucleoside inhibitors (NNIs), that is, residues within at least one atom within a distance of 3.6 Å from the nonnucleoside inhibitor. No mutations were seen for the residues in boldface.

TABLE 2

Residues defining the NNIBP

| Residue Location | nevirapine | 1051U91 | TIBO | -APA | HEPT | compound (I) & (II) |
|---|---|---|---|---|---|---|
| Pro95 β5 | | X | | | | |
| Leu100 β6 | X | X | X | X | X | X |
| Lys101 β6 | | X | X | X | X | |
| Val106 β6 | X | | | | | X |
| Glu138 | | X | | | | |
| β7–β8(p51) | | | | | | |
| Val179 β9 | | | X | X | X | |
| Tyr181 β9 | X | X | X | X | | X |
| Tyr183 β9 | | | | | | X |
| Met184 | | | | | | X |
| β9–β10-turn | | | | | | |
| Asp186 β10 | | | | | | X |
| Tyr188 β10 | X | X | X | X | X | X |
| Val189 β10 | | | | X | | |
| Gly190 β10 | X | | | X | | X |
| Phe227 β12 | X | X | | | X | X |
| Trp229 β12 | | | X | | | X |
| Leu234 β13 | X | | | | X | X |
| His235 β13 | X | | | | | X |
| Tyr318 β15 | X | X | X | X | | X |

Table 3 shows the contribution of individual amino acids in generating binding forces for inhibitor compounds in reverse transcriptase. Among the residues which constitute the overall binding pocket are Leu100, Lys101, Lys103, Val106, Val179, Tyr181, Tyr188, Val189, Gly190, Phe227, Trp229, Leu234, His235, Pro236, and Tyr318.

TABLE 3

| Mutation | Inhibitors | References |
|---|---|---|
| Leu100Ile | Pyridinone | (Byrnes et al., 1993) |
| | BHAP | (Vasudevachari, 1992) |
| | TIBO | (Balzarini et al., 1993) |
| | Nevirapine | (Richman et al., 1993) |
| Lys103Asn | Pyridinone | (Nunberg et al., 1991) |
| | TIBO | (Balzarini et al., 1993) |
| | Nevirapine | (Richman et al., 1993) |
| Val106Ala | BHAP | (Vasudevachari, 1992) |
| | Nevirapine | (Larder, 1992), |
| | | (Richman et al., 1993) |
| | TIBO | (Larder, 1992) |
| Val108Ile | Pyridinone | (Byrnes et al., 1993) |
| | Nevirapine | (Richman et al., 1993) |
| Val179Glu/Asp | Pyridinone | (Byrnes et al., 1993) |
| Tyr181Cys | Nevirapine | (Nunberg et al., 1991), |
| | | (Richman et al., 1991) |
| | TIBO | (Larder, 1992) |
| | Pyridinone | (Byrnes et al., 1993) |
| | BHAP | (Vasudevachari, 1992) |
| | alpha-APA | |
| Tyr188His/Cys | TIBO | (Balzarini et al., 1993) |
| | BHAP | (Demeter et al., 1993) |
| | Nevirapine | (Richman et al., 1993) |
| Gly190Glu | Nevirapine | (Bacolla et al., 1993) |
| Pro236Leu | BHAP | (Dueweke et al., 1993) |
| No Mutations have been seen at the following sites | | |
| Pro95  Phe227  His235 | | |
| Tyr183  Trp229  Tyr318 | | |
| Asp186  Leu234 | | |

Table 4 shows the total energy of complexes and the energy of interactions of a model of nevirapine complexed with reverse transcriptase (Complex O), nevirapine modified with —(CH$_2$)$_4$NH$_2$ complexed with reverse transcriptase ((Complex A)), and nevirapine modified with —(CH$_2$)$_3$NHC(NH)NH$_2$ complexed with reverse transcriptase ((Complex B).

TABLE 4

| | Complex O | Complex A | Complex B |
|---|---|---|---|
| Total Energy of the complexes (Kcal/mol) | | | |
| Bond Stretching Energy | 228 | 224 | 227 |
| Angle Bending Energy | 2129 | 2138 | 2143 |
| Torsional Energy | 1364 | 1372 | 1368 |
| Out of Plane Bending Energy | 76 | 76 | 76 |
| 1–4 van der Waals Energy | 222 | 22.6 | 227 |
| van der Waals Energy | −3303 | −3313 | −3303 |
| 1–4 Electrostatic Energy | 19917 | 19915 | 19903 |
| Electrostatic Energy | −22838 | −22880 | −22940 |
| Total Energy | −2204 | −2239 | −2298 |
| Interaction energy (Kcal/mol) | | | |
| Bond Stretching Energy | 3.4 | 2.0 | 0.7 |
| Angle Bending Energy | −7.3 | 0.1 | 4.5 |
| Torsional Energy | −6.6 | −1.5 | −6.8 |
| Out of Plane Bending Energy | 4.1 | 0.1 | 0.6 |
| 1–4 van der Waals Energy | −1.4 | 0.7 | 1.1 |
| van der Waals Energy | −18.0 | −27.2 | −19.9 |
| 1–4 Electrostatic Energy | 0.0 | −1.6 | −13.4 |
| Electrostatic Energy | 0.0 | 42.1 | −102.6 |
| Total Energy | −30.3 | −73.2 | −137.7 |

Table 5 shows the free energy of solvation for nevirapine complexed with reverse transcriptase (RT-Nevirapine complex), nevirapine modified with —(CH$_2$)$_4$NH$_2$ complexed with reverse transcriptase (RT-Compound A complex), and nevirapine modified with —(CH$_2$)$_3$NHC(NH)NH$_2$ (RT-Compound B complex) complexed with reverse transcriptase.

TABLE 5

Free Energy of Solvation (Kcal/mol)

|  |  | Relative energy |
|---|---|---|
| RT-Nevirapine complex | −7315.1 | 0 |
| RT-Compound A complex | 7340.7 | −25.6 |
| RT-Compound B complex | −7365.7 | −50.6 |

In a specific embodiment, the present invention is directed to a method for designing inhibitors of enzyme human immunodeficiency virus type 1 reverse transcriptase which comprises the steps of:

(a) providing a three dimensional model of the receptor site in the prepolymerization complex of the p66 subunit of enzyme human immunodeficiency virus type 1 reverse transcriptase and a known nonnucleoside inhibitor;

(b) locating the conserved residues in the p66 subunit which constitute the nonnucleoside inhibitor binding pocket; and (c) designing a new nonnucleoside inhibitor which possesses complementary structural features and binding forces to the residues in the p66 subunit nonnucleoside inhibitor binding pocket.

In a preferred embodiment, (i) the three dimensional model in step (a) is the model set out in FIG. 1; (ii) the known nonnucleoside inhibitor in step (a) is selected from the group consisting of alpha-anilinophenylacetamide, bis(heteroaryl)piperazine, nevirapine, and tetrahydroimidazo[4,5,1-jk][1,4]benzodiazepin-2(1H)-one); (iii) the known nonnucleoside inhibitor in step (a) is nevirapine; (iv) the nonnucleoside binding pocket in step (b) comprises residues with at least one atom within a distance of 3.6 Å from the known nonnucleoside inhibitor; (v) the nonnucleoside binding pocket in step (b) comprises residues Leu100, Lys101, Lys103, Val106, Val179, Tyr181, Tyr188, Val189, Gly190, Phe227, Trp229, Leu234, His235, Pro236, and Tyr318; (vi) the nonnucleoside binding pocket in step (b) comprises residues Phe227, Trp229, Leu234, Tyr183, Met184, and Asp186; (vii) the new nonnucleoside inhibitor in step (c) is designed to retain structural and electronic specificity when bound to the conserved residues in the p66 subunit nonnucleoside inhibitor binding pocket; (viii) the new nonnucleoside inhibitor in step (c) is designed to interact with at least one of the three carboxylates in the conserved aspartate residues selected from the group consisting of Asp 110, Asp 185, and Asp 186; (ix) and the conserved aspartate residue is Asp 186.

In another embodiment, the present invention is directed to an inhibitor of enzyme human immunodeficiency virus type 1 reverse transcriptase which comprises a compound represented by the following formula:

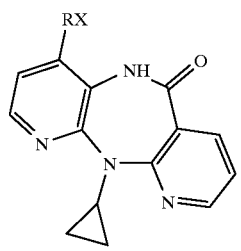

wherein R is an unbranched alkyl or alkenyl group having from 1 to 6 carbon atoms, preferably from 2 to 5 carbon atoms, and more preferably from 4 to 5 carbon atoms, and X is selected from the group consisting of —OH, —NH$_2$, —NHC(NH)NH$_2$ and —PO(OH)$_2$. Preferably, X is —NH$_2$ or —NHC(NH)NH$_2$.

In a preferred embodiment, the inhibitor compound may be represented by the following formula:

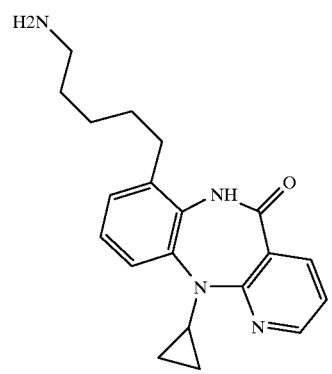

In another preferred embodiment, the inhibitor compound may be represented by the following formula:

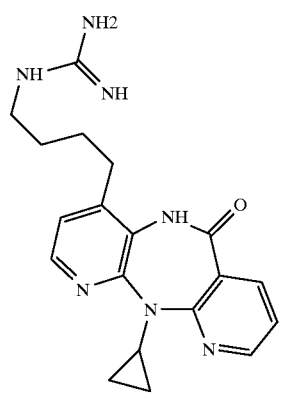

In yet another embodiment, the invention relates to an inhibitor of enzyme human immunodeficiency virus type 1 reverse transcriptase which comprises a compound represented by the following formula:

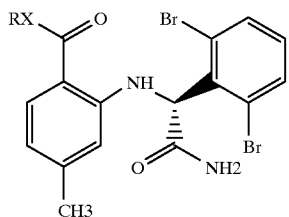

wherein R is an unbranched alkyl or alkenyl group having from 1 to 6 carbon atoms, preferably from 2 to 5 carbon atoms, and more preferably from 4 to 5 carbon atoms, and X is selected from the group consisting of —OH, —NH$_2$, —NHC(NH)NH$_2$ and —PO(OH)$_2$. Preferably, X is —NH$_2$ or —NHC(NH)NH$_2$.

In still yet another embodiment, the invention relates to an inhibitor of enzyme human immunodeficiency virus type 1 reverse transcriptase which comprises a compound represented by the following formula:

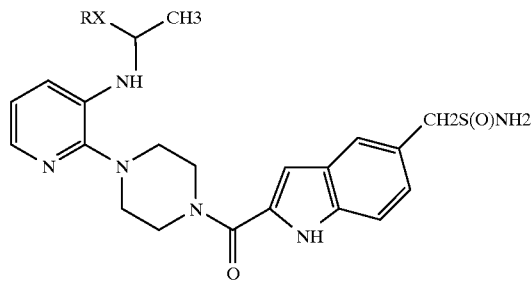

wherein R is an unbranched alkyl or alkenyl group having from 1 to 6 carbon atoms, preferably from 2 to 5 carbon atoms, and more preferably from 4 to 5 carbon atoms, and X is selected from the group consisting of —OH, —NH$_2$, —NHC(NH)NH$_2$ and —PO(OH)$_2$. Preferably, X is —NH$_2$ or —NHC(NH)NH$_2$.

In still yet another embodiment, the invention relates to an inhibitor of enzyme human immunodeficiency virus type 1 reverse transcriptase which comprises a compound represented by the following formula:

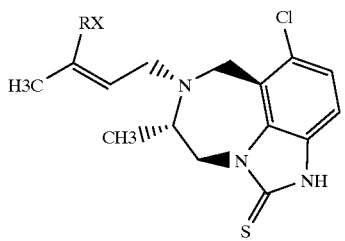

wherein R is an unbranched alkyl or alkenyl group having from 1 to 6 carbon atoms, preferably from 2 to 5 carbon atoms, and more preferably from 4 to 5 carbon atoms, and X is selected from the group consisting of —OH, —NH$_2$, —NHC(NH)NH$_2$ and —PO(OH)$_2$. Preferably, X is —NH$_2$ or —NHC(NH)NH$_2$.

Appendium of References

Bacolla, A., Shih, C.-K., Rose, J. M., Piras, G., Warren, T. C., Grygon, C. A., Ingraham, R. H., Cousins, R. C., Greenwood, D. J., Richman, D., Cheng, Y.-C. & Griffin J. A. (1993). Amino acid substitutions in HIV-1 reverse transcriptase with corresponding residues from HIV-2. *J Biol. Chem.*, 268, 16571–16577.

Balzarini, J., Karlsson, A., Perez-Perez, M.-J., Vrang, L., Walbers, J., Zhang, H., Oberg, B., Vandamme, A.-M., Camarasa, M.-J. & De Clercq, E. (1993). HIV-1specific reverse transcriptase inhibitors show differential activity against mutant strains containing different amino acid substitutions in the reverse transcriptase. *Virology*, 192, 246–253.

Balzarini, J., Karlsson, A., Vandamme, A.-M., Vrang, L., Oberg, B., PerezPerez, M.-J., San-Felix, A., Velazquez, S., Camarasa, M.1. & DeClercq, E. (1992). Noordwijk. in Program and Abstracts-*HIV Drug-Resistance Workshop*, Noordwijk, The Netherlands, Professional Postgraduate Services Europe Ltd.

Balzarini, J., Perez-Perez, M.-J., San-Felix, A., Camarasa, M.-J., Bathurst, I. C., Barr, P. J. & De Clercq, E. (1992). Kinetics of inhibition of human immunodeficiency virus type 1 (HIV-1) reverse transcriptase by the novel HIV-1-specific nucleoside analog [2',5'-bis-O-(tert-butyldimethylsilyl)-β-D-ribofuranosyl]-3'-spiro-5"-(4"-amino-1",2"-oxathiole-2",2"-dioxide)thymine (TSAO-T). *J. Biol. Chem.*, 267, 11831–11838.

Balzarini, J., Perez-Perez, M.-J., San-Felix, A., Schols, D., Perno, C.-F., Vandamme, A.-M., Camarasa, M. J. & De Clercq, E. (1992). 2',5'-bis-O-(tert-butyldimethylsilyl)-3'-spiro-5"-(4"-amino-1",2"-oxathiole-2",2"-dioxide) pyrimidine (TSAO) nucleoside analogues: highly selective inhibitors of human immunodeficiency virus type 1 that are targeted at the viral reverse transcriptase. *Proc. Natl. Acad. Sci. U.S.A.*, 89, 4392–4396.

Bavand, M. R., Wagner, R., & Richmond, T. J., (1993) HIV-1 reverse transcriptase polymerization properties of the p51 homodimeric compared to the p66/p51 heterodimer. *Biochemistry*, 32, 10543–10552.

Boyer, P. L., Tantillo, C., Jacobo-Molina, A.. Manni, R C;.Ding J., Arnold E., and Hughes, S. H., (1994). Selectivety of wild type human immunodeficiency virus type 1 reverse transcriptase to deoxynucleosides depends on template length, the selectivety of drug resistance mutants does not. *Proc. Natn. Acad Sci. U.S.A.*, 91, 4882–4886.

Byrnes, V. W., Sardana, V. V., Schleif, W. A., Condra, J. H., Waterbury, J. A., Wolfgang, J. A., Long, W. J., Schneider, C. L., Schlabach, A. J., Wolanski, B. S., Graham, D. A., Gotlib, L., Rhodes, A., Titus, D. L., Roth, E., Blahy, O. M., Quintero, J. C., Staszewski, S. & Emini, E. A. (1993). Comprehensive mutant enzyme and viral variant assessment of human immunodeficiency virus type 1 reverse transcriptase resistance to nonnucleoside inhibitors. *Antimicrob. Agents Chemother.*, 37, 1576–1579.

Demeter, L., Resnick, L., Nawaz, T., Timpone, J. G., Jr., Batts, D. & Reichman, R. C. (1993). Phenotypic and genotypic analysis of ateviridine (ATV) susceptibility of HIV-1 isolates obtained from patients receiving ATV monotherapy in a phase I clinical trial (ACTG 187): comparison to patients receiving combination therapy with ATV and zidovudine. *Third Workshop on Viral Resistance*, Gaithersburg, Md., USA, Ding, J., Das, K., Moereels, H., Koymans, L., Andries, K., Janssen, P. A. J., Hughes, S. H. & Arnold, E. (1995A). Structure of HIV-1 RT/TIBO R 86183 reveals similarity in the binding of diverse nonnucleoside inhibitors. *Nature Structural Biology*, 2, 407–415.

Ding, J., Das, K., Tantillo, C., Zhang, W., Clark, A. D., Jr., Jessen, S., Lu, X., Hsiou, Y., Jacobo-Molina, A., Andries, K., Pauwels, R., Moereels, H., Koymans, L., Janssen, P. A. J., Smith, R., Koepke, M. K., Michejda, C., Hughes, S. H. & Arnold, E. (1995B). Structure of HIV-1 reverse transcriptase in a complex with the nonnucleoside inhibitor alpha-APA R 95845 at 2.8 Å resolution. *Structure*, 3, 365–379.

Dueweke, T. J., Pushkarskaya, T., Poppe, S. M., Swaney, S. M., Zhao, J. Q., Chen, I. S. Y., Stevenson, M. & Tarpley, W. G. (1993). A mutation in reverse transcriptase of bis(heteroaryl)piperazine-resistant human immunodeficiency virus type 1 that confers increased sensitivity to other nonnucleoside inhibitors. *Proc. Natl. Acad. Sci. U.S.A.*, 90, 4713–4717.

Fitzgibbon, J. E., Farnham, A. E., Sperber, S. J., Kim, H., and Dubin, D. T., (1993). Human Immunodeficiency Virus type 1 pol 1 gene mutations in an AIDS patient treated with multiple antiretrpviral drugs. *J. Virol.*, 67, 7271–7Z75.

Furfine, E. S. & Reardon, J. E. (1991). Human immunodeficiency virus reverse transcriptase ribonuclease H: specificity of tRNA-Lys3-primer excision. *Biochemistry*, 30, 7041–7046.

Goff, S. P. (1990). Retroviral reverse transcriptase: synthesis, structure, and function. *J of Acquired Immune Deficiency Syndromes*, 3, 817–831.

Jacques, P. S., Wohrl, B. M., Ottmann, M., Darlix, J. L. & Le Grice, S. F. J. (1994). Mutating the "primer grip" of p66 HIV-1 reverse transcriptase implicates tryptophan-229 in template-primer utilization. *J. Biol. Chem.*, 269, 2647226478.

Jacobo-Molina, A., Ding, J., Nanni, R. G., Clark, A. D, J, Lu, X., Tantillo, C., Williams, R. L., Kamer, G., Ferris, A. L., Clark, P., Hizi, A., Hughes, S. H., & Arnold, E. Crystal structure of human immunodeficiency virus type 1 reverse transcriptase complexed with double-stranded DNA at 3.0 Å resolution shows bent DNA. *Proc. Natn. Acad. Sci. U.S.A.*, 90, 6320–6324 (1993).

Johnson, M. S., McClure, M. A., Feng, D., Gray, J. & Doolittle, R. F. (1986). Computer analysis of retroviral pol genes: assignment of enzymatic functions to specific sequences and homologies with nonviral enzymes. *Proc. Natl. Acad. Sci. U.S.A.*, 83, 7648–7652.

Kellam, R., Boucher, C. A. B. & Larder, B. A., (1992). Fifth mutation in human immunodeficiency virus type 1 reverse transcriptase contributes to the development of high-level resistance to zidovudine. *Proc. Natn. Acad Sci. U.S.A.*, 89, 1934–1938.

Kew, Y., Qingbin, S., & Prasad, V. R., (1994). Subunit-selective mutagenesis of Glu89 residue in human immunodeficiency virus reverse transcriptase. *J. Biol. Chem.*, 269, 15331–15336.

Kleim, J.-P., Bender, R., Billhardt, U.-M., Meichsner, C., Riess, G., Rosner, M., Winkler, I. & Paessens, A. (1993). Activity of a novel quinoxaline derivative against human immunodeficiency virus type 1 reverse transcriptase and viral replication. *Antimicrob. Agents Chemother.*, 37, 1659–1664.

Lacey, S. F., Reardon, J. E., Furfine, E. S., Kunkel, T. A., Bebenet. K., Eckert, K. A., Kemp, S. D., & Larder, B. A., (1992). Biochemical studies on the reverse transcriptase and RNase H activities from human immunodeficiency virus strains resistant to 3'-azido-3'-deoxythymidine. *J. Bio. Chem.* 267, 15789–15794.

Lacey, S. F., and Larder, B. A., (1994). Mutagenesis study of codon 74 and 215 of the humnan immunodeficiency virus type 1 reverse transcriptase, which are significant in nucleoside analog resistance. *J. Virol.*, 68, 3421–3424.

Larder, B. A., Darby, G., & Richman, D. D. (1989). HIV with reduced sensitivity to Zidovudine (AZT) Isolated During Prolonged Therapy. *Science*, 243, 1731–1734.

Larder, B. A. (1992). AZT resistance suppressed by a mutation conferring HIV1 resistance to non-nucleoside reverse transcriptase inhibitors. *Antimicrob. Agents Chemother.*, 36, 1171–1174.

Larder, B. A. (1993). Inhibitors of HIV reverse transcriptase as antiviral agents and drug resistance. In *Reverse Transcriptase* (A. M. Skalka & S. P. Goff, ed., pp. 205–222, Cold Spring Harbor Laboratory Press, Plainview, N.Y.

Martin, J. L., Wilson, J. E., Haynes, R. L. & Furnan, P. A. (1993). Mechanism of human immunodeficiency virus type 1 resistance to dideoxyinosine. *Proc. Natn. Acad. Sci. U.S.A.*, 90, 6134–6139.

Nunberg, J. H., Schleif, W. A., Boots, E. J., O'Brien, J. A., Quintero, J., Hoffinan, J. M., Goldman, M. E. & Emini, E. A. (1992). Noordwijk. In Program and Abstracts-*HIV Drug-Resistance* Workshop, Noordwijk, The Netherlands, Professional Postgraduate Services Europe Ltd.

Nunberg, J. H., Schleif, W. A., Boots, E. J., O'Brien, J. A., Quintero, J. C., Hoffinan, J. M., Emini, E. A. & Goldman, M. E. (1991). Viral resistance to human immunodeficiency virus type 1-specific pyridinone reverse transcriptase inhibitors. *J. Virol.*, 65, 4887–4892.

Pauwels, R., Andries, K., Debyser, Z., Kulda, M. J., Schols, D., Breslin, H. J., Woestenborghs, R., Desmyter, J., Janssen, M. A. C., De Clercq, E. & Janssen, P. A. J. (1994). New TIBO derivatives are potent inhibitors of HIV-1 replication and are synergistic with 2',3'-dideoxynucleoside analogues. *Antimicrobial agents and Chemotherapy*, 38, 2863–2870.

Pauwels, R., Andries, K., Desmyter, J., Schols, D., Kukla, M. J., Breslin, H. J., Raeymaeckers, A., Van Gelder, J., Woestenborghs, R., Heykants, J., Schellekens, K., Janssen, M. A. C., De Clercq, E. & Janssen, P. A. J. (1990). Potent and selective inhibition of HIV-1 replication in vitro by a novel series of TTT30 derivatives. *Nature*, 343, 470–474.

Pelletier, H., Sawaya, M. R., Kumar, A., Wilson, S. H., and Kraut, J. (1994). Structures of ternary complexes of rat DNA polymerase B, a DNA template-primate, and ddCTP. *Science*, 264, 18911903.

Plaxco, K. W. a. G., W. A. (1994). Contribution of the thymine methyl group to the specific recognition of poly- and mononucleotides: An analysis of the relative free energies of solvation of thymine and uracil. *Biochemistry*, 33, 3050–3054.

Ren, J., Esnouf, R., Garman, E., Somers, D., Ross, C., Kirby, I., Keeling, J., Darby, G., Jones, Y., Stuart, D. & Stammers, D. (1995). High resolution structures of HIV-1 RT from four RT-inhibitor complexes. *Nature Structural Biology*, 2, 293–302.

Richman, D., Shih, C. K., Lowy, I., Rose, J., Prodanovich, P., Goff, S. & Griffin, J. (1991). Human immunodeficiency virus type 1 mutants resistant to non-nucleoside inhibitors of reverse transcriptase arise in tissue culture. *Proc. Natl. Acad. Sci. U.S.A.*, 88, 11241–11245.

Richman, D. D., Havlir, D., Corbeil, J., Looney, D., Ignacio, C., Spector, S. A., Sullivan, J., Cheeseman, S., Barringer, K., Pauletti, D., Shih, C.-K., Myers, M. & Griffin, J. (1993). Nevirapine resistance mutations of HIV-1 selected during therapy. (submitted), Rodgers, D. W., Gamblin, S. J., Harris, B. A., Ray, S., Culp, J. S., Hellmig, B., Woolf, D. J., Debouck, C. & Harrison, S. C. (1995). The structure of unliganded reverse transcriptase from the human immunodeficiency virus type 1. *Proc. Natl. Acad Sci. U.S.A.,* 22, 1222–1226.

Schleif, W. A., Emini, E. A., Rhodes, A., Titus) D. L., Gotlib, L., Condra, J. H. & Byrnes, V. W. (1992). Development and analysis of human immunodeficiency virus type 1 resistant to HIV-1 specific pyridinone reverse transcriptase inhibitors. *J. Cell. Biochem., Suppl.,* 16E, 87.

Schreiber, S. L., *Chemical & Engineering News,* pp 22–32, Oct. 26, 1992.

Shafer, R. W., Kozal, M. J., Winters, M., Iversen, A. K. N., Katenstein, D. A., Ragni, M. V., Meyer, W. A. I., Gupta, P., Rasheed, S., Coombs R., Katzman, M., Fiscus. S., & Merigan, T. C.,. (1994). *J. Infect. Diseases,* 169, 722–729.

Smerdon, S. J., Jager, J., Wang, J., Kohlstaedt, L. A., Chirino, A. J., Friedman, J. M., Rice, P. A. & Steitz, T. A. (1994). Structure of the binding site for nonnucleoside inhibitors of the reverse transcriptase of human immunodeficiency virus type 1. *Proc. Natl. Acad Sci. U.S.A.,* 91, 3911–3915.

St. Clair, M. H., Richards C. A., Spector, T, Weinhold, K. J., Miller, W.H, Langlois A. J., and Funnan, P.A., (1987). 3'-azido-3'-deoxythymidine triphosphate as an inhibitor and substrate of purified human immunodeficiency virus type 1. *Antimicrobial Agents Chemother.,* 31, 1972–1977.

Vasudevachari, M. B., Battista, C., Lane, H. C., Psallidopoulos, M. C., Zhao, B., Cook, J., Palmer, J. R., Romero, D. L., Tarpley, W. G. & Salzman, N. P. (1992). Prevention of the spread of HIV-1 infection with nonnucleoside reverse transcriptase inhibitors. *Virology,* 190, 269–277.

Yadav, P. N. S., Yadav, J. S., & Modak, M. J., (1992). A molecular model of the complete three dimensional structure of the Kienow fragment of *E. coli* DNA polymerase I: Binding of the dNTP substrate and template-primer. *Biochemistry,* 31, 2879–2886 (1992).

Yadav, P. N. S., Yadav, J. S., & Modak, M. J., (1995). Nucleoside drug resistance in HIV-1 resistance transcriptase. *Structural Biology,* 2, 193–195.

The invention being thus described, it will be obvious that the same may be varied in many ways. Such variations are not to be regarded as a departure from the spirit and scope of the invention and all such modifications are intended to be included within the scope of the following claims.

We claim:

1. A compound represented by the following formula:

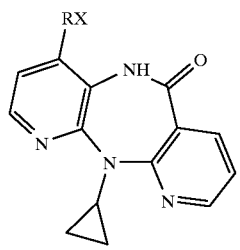

wherein R is an unbranched alkyl or alkenyl group having from 1 to 6 carbon atoms, and X is selected from the group consisting of —NH$_2$, —NHC(NH)NH$_2$ and —PO(OH)$_2$.

2. A compound according to claim 1, wherein R is from 2 to 5 carbon atoms.

3. A compound according to claim 2, wherein R is from 4 to 5 carbon atoms.

4. A compound according to claim 1, wherein X is —NH$_2$.

5. A compound according to claim 1, wherein X is —NHC(NH)NH$_2$.

6. A compound according to claim 1, wherein the compound may be represented by the following formula:

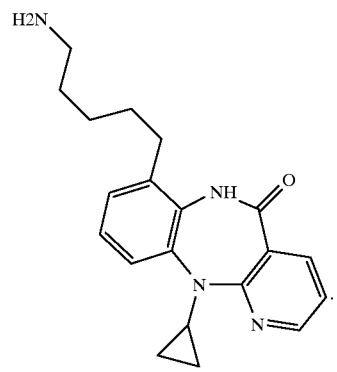

7. A compound according to claim 1, wherein the compound may be represented by the following formula:

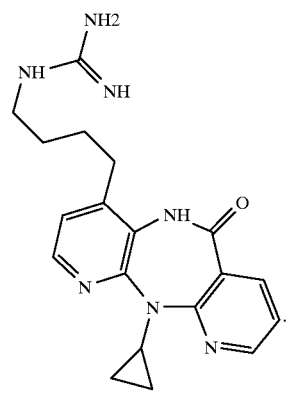

* * * * *